(12) United States Patent
Kanao

(10) Patent No.: US 7,484,402 B2
(45) Date of Patent: Feb. 3, 2009

(54) GAS SENSOR

(75) Inventor: Keiji Kanao, Chita-gun (JP)

(73) Assignee: Denso Corporation (JP)

( * ) Notice: Subject to any disclaimer, the term of this patent is extended or adjusted under 35 U.S.C. 154(b) by 180 days.

(21) Appl. No.: 11/607,014

(22) Filed: Dec. 1, 2006

(65) Prior Publication Data

US 2007/0131022 A1    Jun. 14, 2007

(30) Foreign Application Priority Data

Dec. 14, 2005   (JP) .............................. 2005-360384

(51) Int. Cl.
*G01N 27/00* (2006.01)
*G01M 15/10* (2006.01)

(52) U.S. Cl. ..................... 73/31.05; 73/23.31

(58) Field of Classification Search ............... 73/23.31, 73/31.05
See application file for complete search history.

(56) References Cited

U.S. PATENT DOCUMENTS 2,065,404 A * 12/1936 Scott ........................ 428/428
2,371,627 A *  3/1945 Kingston .................... 428/433
2,502,855 A *  4/1950 Kingston .................... 148/286
3,185,597 A *  5/1965 Altman ...................... 148/621
3,526,550 A *  9/1970 Larson et al. .............. 428/472.1
4,695,333 A *  9/1987 Inoue et al. ................ 148/306
5,698,084 A * 12/1997 Weyl et al. ................. 204/424
6,096,181 A *  8/2000 Friese et al. ............... 204/424
6,623,612 B2   9/2003 Shirai ........................ 204/424

FOREIGN PATENT DOCUMENTS

JP       62-297246 A  * 12/1987
JP        1-275741 A  * 11/1989

* cited by examiner

*Primary Examiner*—Daniel S Larkin
(74) *Attorney, Agent, or Firm*—Nixon & Vanderhye PC

(57) ABSTRACT

A gas sensor having a housing, a first insulation porcelain, a metal sealing member interposed between a seat surface of the housing and a contacting surface of the first insulation porcelain. The metal sealing member is made of a Fe-based alloy of containing 10 wt % or less Cr.

4 Claims, 6 Drawing Sheets

GAS SENSOR

CROSS REFERENCE TO RELATED APPLICATION

This application is based on Japanese Patent Application No. 2005-360384 filed on Dec. 14, 2005, the disclosure of which is incorporated herein by reference.

FIELD OF THE INVENTION

The present invention relates generally to a sensor that may be installed in the exhaust system of an internal combustion engine for air fuel ratio control.

BACKGROUND OF THE INVENTION

As shown in FIG. 7, a gas sensor 9 is known which inserting a sensor element 911 into first insulation porcelain 912 assembles and then mounting the first insulation porcelain 912 in a housing 913.

The sensor element 911 has a measuring electrode exposed to measurement gas and a reference electrode exposed to reference gas. The sensor element 911 determines a concentration of a particular gas by providing a signal in the form of an ion current flowing through the measuring electrode and the reference electrode or of a potential difference between the measuring electrode and the reference electrode.

A gas leak from a measurement gas chamber 915 to an air chamber 914 will result in a decrease the accuracy of measuring the concentration of the particular gas.

In Japanese Patent Laid-open Publication No. 2002-82085, it is described that the gas sensor 9 has the first insulation porcelain 912 carried on the housing 913 via a metal packing ring 92.

As shown in FIGS. 7 and 8, a seat surface 917 formed on an inside surface of the housing 913 supports a contacting surface 916 formed on an outside surface of the first insulation porcelain 912 via the metal packing ring 92. Specifically, a gap between the seat surface 917 of the housing 913 and the contacting surface 916 of the first insulation porcelain 912 is sealed hermetically by the metal packing ring 92 to keep the air chamber 914 and the gas chamber 915 airtight.

More recently, however, since engines are required to have lower fuel consumption and higher output power for protecting the environment, the temperature of the exhaust gas has increased. When the gas sensor 9 is exposed to the high temperature, the temperature of the metal packing ring 92 rises, too. After the gas sensor 9 is used many times, as shown in FIG. 8, an oxidized corrosion 920 becomes in the whole metal packing ring 92 and then the durability of the metal packing ring 92 deteriorates. Therefore, there is the concern that the gap between the air chamber 914 and the gas chamber 915 can not be sufficiently hermetically sealed by the metal packing ring 92.

SUMMARY OF THE INVENTION

In view of the above-described problems, it is an object of the present invention to provide an improved structure of a gas sensor that provides a mechanical seal required to keep an air chamber and a measurement gas chamber in the gas sensor highly airtight.

This object can be achieved by providing a gas sensor comprising: a gas sensing element detecting a concentration of a particular gas contained in measurement gas; a first insulation porcelain holding therein said gas sensing element; a housing holding said first insulation porcelain on an inner surface thereof; a seat surface formed on said inner surface of said housing receiving a contacting surface formed on an outside surface of said first insulation porcelain; and a metal sealing member interposed between said seat surface of said housing and said contacting surface of said first insulation porcelain to hermetically define an air chamber in which a base end side of said gas sensing element is disposed and a measurement gas chamber in which a top end side of said gas sensing element is disposed, and wherein said metal sealing member is made of a Fe-based alloy containing 10 wt % or less Cr.

This object can also be achieved by providing a gas sensor comprising: a gas sensing element detecting a concentration of a particular gas contained in a measurement gas; a housing holding said gas sensing element; a seat surface formed on an inner surface of said housing receiving a contacting surface formed on an outside surface of said gas sensing element; and a metal sealing member interposed between said seat surface of said housing and said contacting surface of said gas sensing element to hermetically define an air chamber in which a base end side of said gas sensing element is disposed and a measurement gas chamber in which a top end side of said gas sensing element is disposed, wherein said metal sealing member is made of a Fe-based alloy containing 10 wt % or less Cr.

This object can also be achieved by providing a gas sensor comprising: a gas sensing element detecting a concentration of a particular gas contained in measurement gas; a first insulation porcelain holding therein said gas sensing element; a housing holding said first insulation porcelain on an inner surface thereof; a seat surface formed on said inner surface of said housing receiving a contacting surface formed on an outside surface of said first insulation porcelain; and a metal sealing member interposed between said seat surface of said housing and said contacting surface of said first insulation porcelain to hermetically define an air chamber in which a base end side of said gas sensing element is disposed and a measurement gas chamber in which a top end side of said gas sensing element is disposed, said metal sealing member having an oxidized layer that comprises a chrome oxide layer and a ferric oxide layer, and that is at least 5 μm thick after said metal sealing member is exposed to environmental conditions as follows: a cycle of changing temperature from 300° C. or less to 600° C. or more that is repeated 1000 times or more and total hours at 600° C. or more is fifty hours or more.

The invention may also be embodied in a gas sensor comprising: a gas sensing element detecting a concentration of a particular gas contained in measurement gas; a housing holding said gas sensing element; a seat surface formed on an inner surface of said housing receiving a contacting surface formed on an outside surface of said gas sensing element; and a metal sealing member interposed between said seat surface of said housing and said a contacting surface of said gas sensing element to hermetically define an air chamber in which a base end side of said gas sensing element is disposed and a measurement gas chamber in which a top end side of said gas sensing element is disposed; said metal sealing member having an oxidized layer that comprises a chrome oxide layer and a ferric oxide layer and that has a thickness of at least 5 μm after said metal sealing member is exposed to environmental conditions as follows: a cycle of changing temperature from 300° C. or less to 600° C. or more that is repeated 1000 times or more and total hours at 600° C. or more is fifty hours or more.

BRIEF DESCRIPTION OF THE DRAWINGS

Other objects, features and advantages of the present invention will become more apparent from the following detailed description made with reference to the accompanying drawings, in which.

DETAILED DESCRIPTION OF THE PREFERRED EMBODIMENTS

In this application, the installed side in an exhaust pipe of an internal combustion engine is defined as the top end side, the other side of the top end side is defined as the base end side.

Example 1

Figure 1:
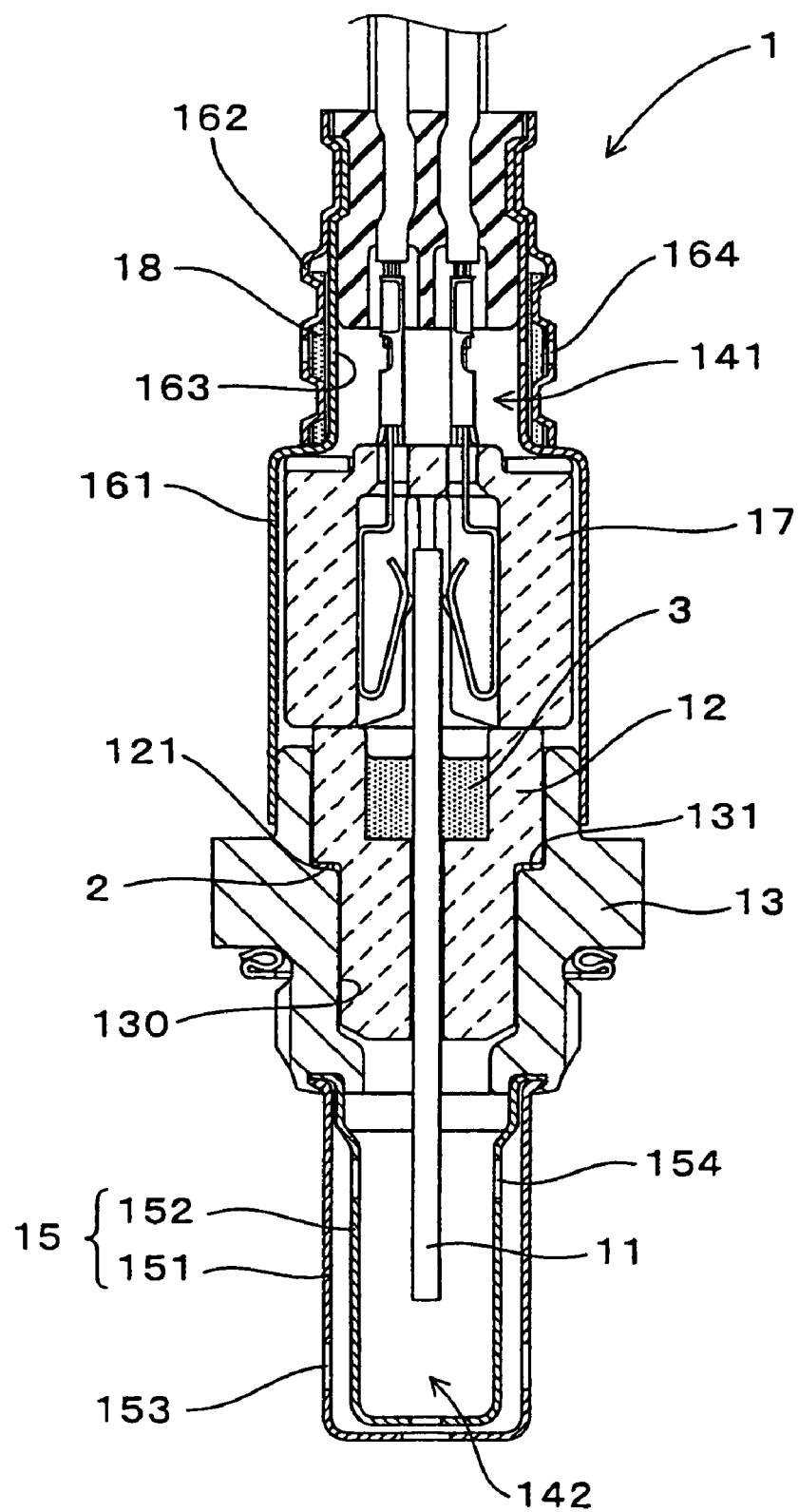
FIG. 1 is a longitudinal sectional view that shows a gas sensor according to a first example embodiment of the present invention.
Figure 2:
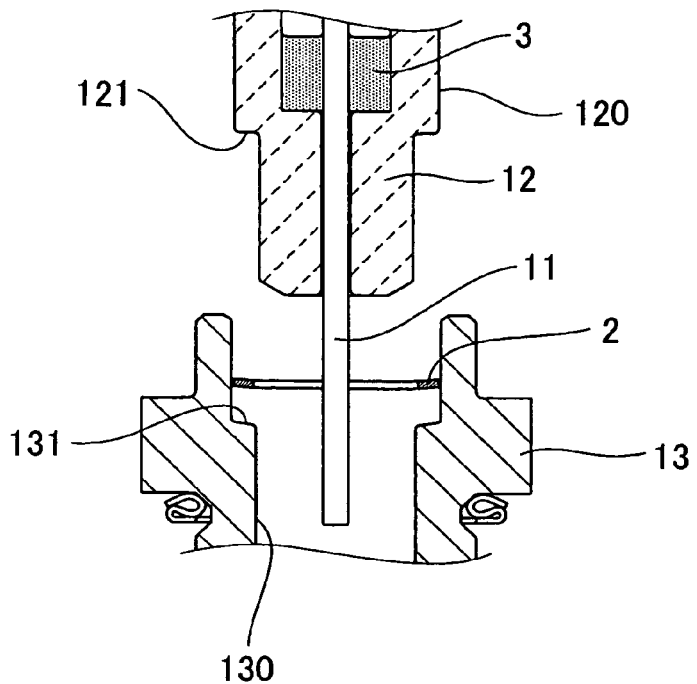
FIG. 2 illustrates a metal packing ring, a first insulation porcelain and a housing of the gas sensor of FIG. 1.
Figure 3:
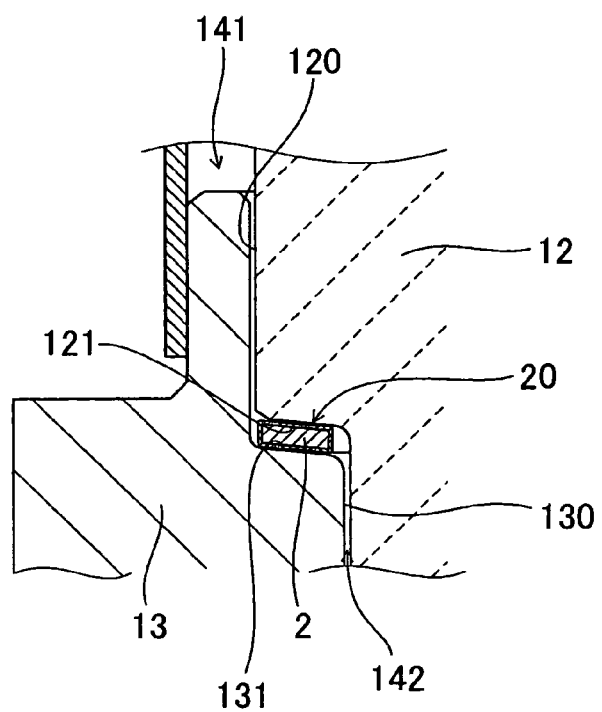
FIG. 3 schematically illustrates, in cross section, the metal packing ring between the first insulation porcelain and the housing of FIG. 1.

Referring to the drawing, wherein like reference numbers refer to like parts in the several views, particularly to FIGS. 1-3, there is shown a gas sensor 1 according to a first example embodiment of the invention.

The gas sensor 1 may be employed in an air-fuel ratio control system for a component such as NOx, CO, HC, or O2 contained in exhaust gases of the engine.

The gas sensor 1 includes a gas sensing element 11 detecting a concentration of particular gas contained in measurement gas, a first insulation porcelain 12 holding therein the gas sensing element 11 and a housing 13 holding the first insulation porcelain 12 on the inner surface 130 thereof. An air cover 161 is disposed on the base end side of the housing 13, a measurement gas cover 15 is disposed on the top end side of the housing 13, and a second insulation porcelain 17 is disposed in the air cover 161. Furthermore, the second insulation porcelain 17 is disposed on the base end side of the first insulation porcelain 12.

As shown in FIG. 1, an outer side cover 162 is provided around the outside of the base end side of the air cover 161 via an air permeability filter 18. Air vents 163 and 164 are formed in the cover 161 and the outer side cover 162 for introducing a reference gas into an air chamber 141 surrounded by the air cover 161.

Furthermore, the reference gas is introduced into a reference gas chamber formed in the gas sensing element 11 through the second insulation porcelain 17.

On the other hand, the measurement gas cover 15 consists of an outer cover 151 and an inner cover 152. Gas holes 153 and 154 are formed in the outer cover 151 and the inner cover 152 to introduce measurement gas into a measurement gas chamber 142 surrounded by the inner cover 152. Furthermore, the measurement gas is introduced into a measurement gas chamber (not shown) formed in the gas sensing element 11.

A reference electrode is exposed to reference gas in the reference gas chamber of the gas sensing element 11 and a measuring electrode is exposed to measurement gas in the measurement gas chamber of the gas sensing element 11.

The gas sensor 1 provides a signal in the form of an ion current flowing or a potential difference between the measuring and the reference electrodes to determine the concentration of a particular gas. Thus, it is important that the seal be hermetic to keep the air chamber 141 of the base end side of the gas sensor 1 and the measurement gas chamber 142 of the top end side of the gas sensor 1 airtight.

A seat surface 131 to receive a contacting surface 121 formed on the first insulation porcelain 12 is formed on the inner surface 130 of the housing 13. A metal sealing member 2, such as metal a packing ring, is interposed between the seat surface 131 of the housing 13 and the contacting surface 121 of the first insulation porcelain 12. Furthermore, the metal sealing member 2 hermetically defines the air chamber 141 in which the base end side of the gas sensing element 11 is disposed and the measurement gas chamber 142 in which the top end side of the gas sensing element 11 is disposed.

Furthermore, a glass sealing member 3 air-tightly seals between the first insulation porcelain 12 and the gas sensing element 11, thereby the glass sealing member 3 hermetically seals to keep the air chamber 141 and the measurement gas chamber 142 airtight with the metal sealing member 2.

As shown in FIG. 2, the method of manufacturing the gas sensor 1 will be described as follows. The top end side of the first insulation porcelain 12 which holds the gas sensing element 11 is inserted into the ring shaped metal sealing member 2 at first and then the first insulation porcelain 12 is inserted into the housing 13. After that, the base surface of the metal sealing member 2 and the first insulation porcelain 12 and the top surface of the metal sealing member 2 and the seat surface 131 of the housing 13, are disposed to closely contact.

In this example, the metal sealing member 2 is made of a Fe-based alloy containing 1-10 wt % of Cr. The amount ratio of Fe to the gross weight of the metal sealing member is 50 wt % or more.

As shown in FIG. 3, the metal sealing member 2 has an oxidized layer 20 formed on the surface of the metal sealing member 2 to a thickness of at least 5 μm, after the metal sealing member 2 is exposed to environmental conditions as follows: a cycle of changing temperature from 300° C. or less to 600° C. or more repeated 1000 times or more and total hours at 600° C. or more is fifty hours or more. The oxidized layer 20 is comprised of a chrome oxide layer and a ferric oxide layer formed behind the chrome oxide layer. The ratio of the area of 5 μm or more of thickness of the oxidized layer 20 to the gross area of the contact surfaces, between the metal sealing member 2 and the first insulation porcelain 12 or between the metal sealing member 2 and the housing 13, is 30% or more.

As a consequence, since the oxidized layer 20 is sufficiently formed on the contact surface, the layer 20 can sufficient provide the function of this invention.

Next, the function and result of this example will be described.

The metal sealing member 2 is made of an alloy of Fe and 1-10 wt % of Cr. As such, even though the gas sensor 1 is exposed to the high temperature, as shown in FIG. 3, an oxidized layer 20 which comprises the chrome oxide layer and the ferric oxide layer is formed on the surface of the metal sealing member 2. Therefore, the metal sealing member 2 can be protected by the oxidized layer 20 and can be prevented from developing oxidized corrosion. Furthermore, the contact between the metal sealing member 2 and the first insulation porcelain 12 or the contact between the metal sealing member 2 and the housing 13 can be kept airtight.

Furthermore, even though the gas sensor 1 is exposed to the above-mentioned conditions, the oxidized layer of the metal sealing member 2 has a thickness of 5 µm or more. Therefore, even when the gas sensor 1 is installed in the exhaust system of an internal combustion engine, the oxidized layer 20 can sufficiently protect the sealing metal member 2. Furthermore, the contact between the metal sealing member 2 and the first insulation porcelain 12 or the contact of the metal sealing member 2 and the housing 13 can be sufficiently ensured to keep the sealing property.

As mentioned above, this invention can provide the gas sensor 1 which can avoid failure of the hermetic seal that keeps the air chamber 141 of the base end side of the sensor element 11 and the measurement gas chamber 142 of the top end side of the sensor element 11 airtight.

Example 2

Figure 4:
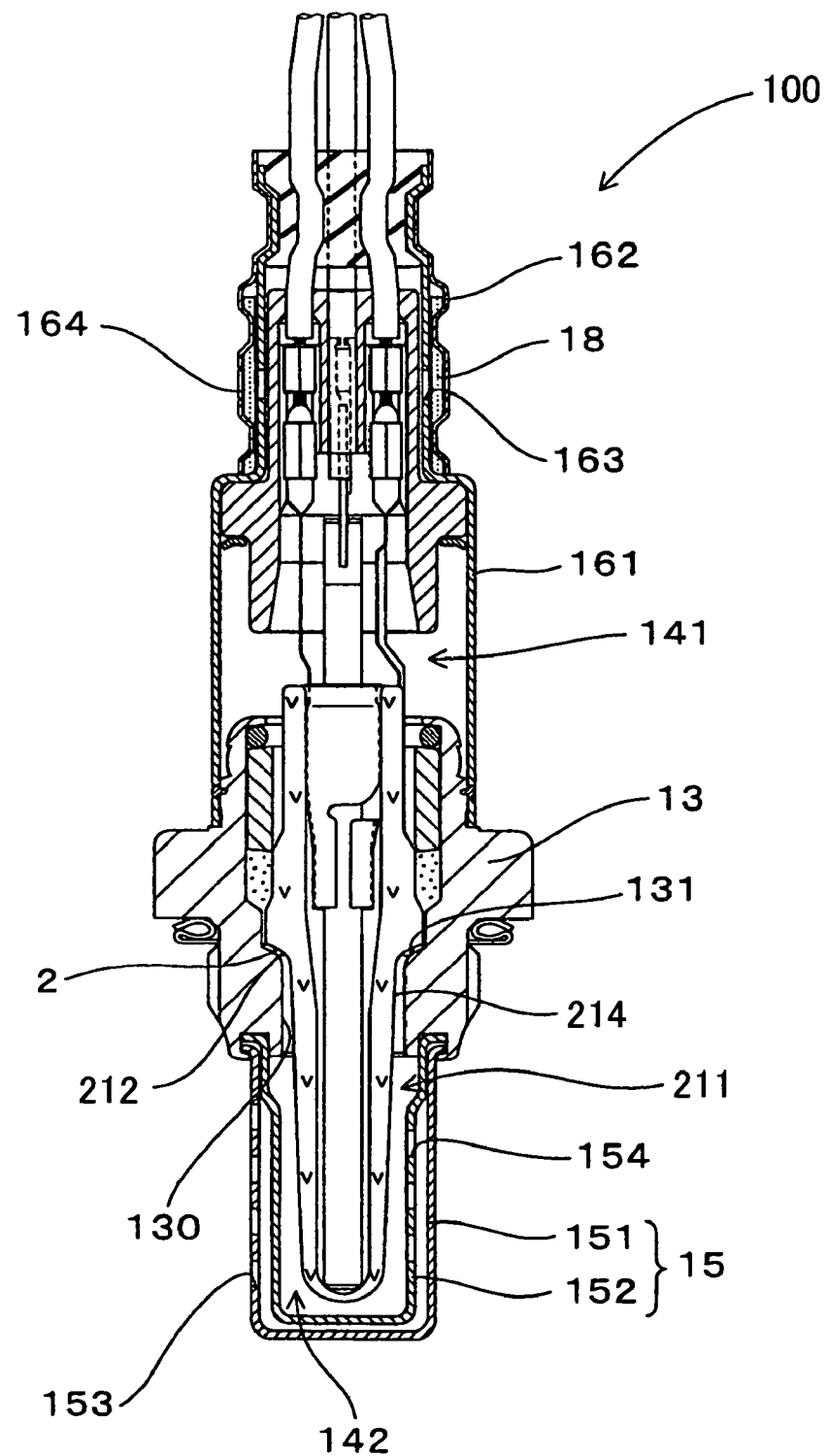
FIG. 4 is a longitudinal sectional view of a gas sensor according to a second example embodiment of the present invention.

In this Example, as shown in FIG. 4, the gas sensor 100 includes a hollow-shape gas sensing element 211 having a closed portion at the end thereof, and a housing 13 holding the gas sensing element 211.

A contact surface 212 is formed on the outer surface 214 of the gas sensing element 211 to be received on the seat surface 131 of the housing 13. A metal sealing member 2 is interposed between the seat surface 131 of the housing 13 and the contact surface 212 of the sensor element 211.

In this example, since the durability of the metal sealing member 2 can be maintained by forming the oxidized layer, the air tightness between the housing 13 and the sensor element 211 can be ensured.

Otherwise the composition, function and result of this example embodiment are the same as Example 1.

Example 3

Figure 5:
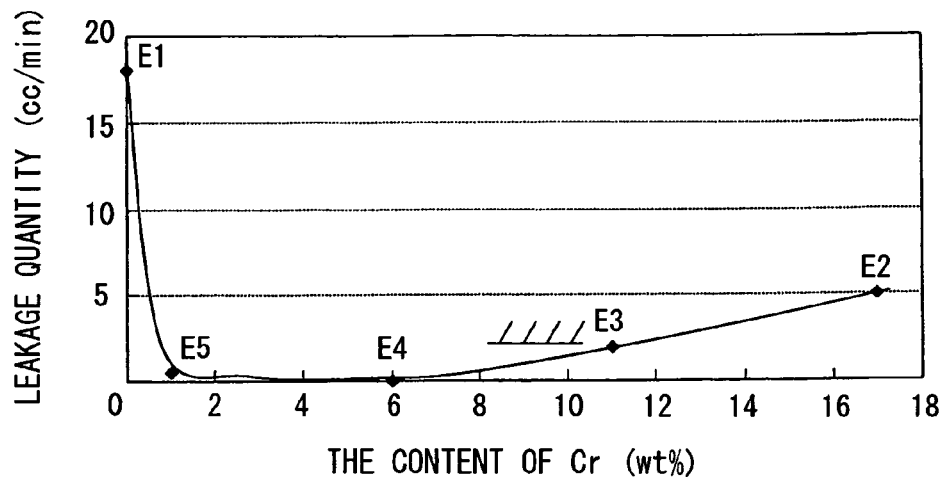
FIG. 5 is a graph representing a relationship between the leakage quantity of measurement gas and content of Cr included in a metal sealing member according to a third example embodiment of the present invention.

FIG. 5 is a graph representing a relationship between the leakage quantity of gas from the measurement gas chamber 142 to the air chamber 141 and the content of Cr in the metal sealing member after carrying out a heat-cold endurance test.

As shown in TABLE. 1, various metal sealing members, which are identified such as SAMPLES E1-E5, are disposed in the gas sensor 1. Sample E1 is a metal sealing member consisting of Fe, sample E2 is a metal sealing member consisting of 83 wt % Fe and 17 wt % Cr, sample E3 is a metal sealing member consisting of 89 wt % Fe and 11 wt % Cr, sample E4 is a metal sealing member consisting of 52 wt % Fe, 42 wt % Ni and 6 wt % Cr, and sample E5 is a metal sealing member consisting of 99 wt % Fe and 1 wt % Cr.

The sizes of the metal sealing members of each sample are as follows: the outer diameter is 14.5 mm, the inner diameter is 12.0 mm, the thickness is 0.4 mm.

TABLE 1

| | (wt %) | | |
| --- | --- | --- | --- |
| | Fe | Ni | Cr |
| SAMPLE E1 | 100 | — | — |
| SAMPLE E2 | 83 | — | 17 |
| SAMPLE E3 | 89 | — | 11 |
| SAMPLE E4 | 52 | 42 | 6 |
| SAMPLE E5 | 99 | — | 1 |

The conditions of the heat-cold endurance, test are as follows: the gas sensors 1 are heated for six minutes so that the maximum temperature of the housing 13 of the gas sensors 1 is 650° C. and then the gas sensors 1 are cooled for four minutes so that the minimum temperature of the housing 13 of the gas sensors 1 is 150° C. This process from heating to cooling is regarded as one cycle. The cycle is carried out 1000 times. In this case of the above heating, the gas sensors 1 are exposed to 600-650° C. for fifty hours or more.

After the gas sensors 1 receive the heat-cold endurance test, the gas sensors 1 are installed in a leak check apparatus for an air tightness test and the leakage quantity of gas from the measurement gas chamber 142 to the air chamber 141 per minute is measured in the high temperature environment (the temperature of the flange of the housing 13 is about 650° C.)

FIG. 5 depicts the relationship between the content of Cr and the leakage quantity (SAMPLE E1-E5). Ten samples of each sample type were tested and the maximum value of each sample type are plotted in FIG. 5.

As illustrated, the leakage quantity of the SAMPLE E1 is too large, since it is above 2 cc/min. The leakage quantity of SAMPLE E2 is also too large, since it is above 2 cc/min. On the other hand, the leakage quantity of SAMPLE E4-E5 is small, as it is below 2 cc/min.

More specifically, when the amount of Cr in the metal sealing member 2 is more than 10 wt %, there is a concern that the thickness of the oxidized layer will be too thin. In this case, even though a thin film oxidized layer 20 can prevent the oxidized corrosion of the metal sealing member 2 from developing, there is a concern that the contacting property between the metal sealing member 2 and the first insulation porcelain 12 may be unable to be ensured because of the development of the oxidized corrosion. Consequently, the oxidized layer may be unable to sufficiently prevent failure of sealing contact between the air chamber 141 and the measurement gas chamber 142 through sealing member 2.

On the other hand, when the amount of Cr in the metal sealing member is less than 1 wt %, it is difficult for the oxidized layer 20 to be fully formed on the surface of the metal sealing member 2, and oxidized corrosion of the sealing member 2 can easily proceed. As a consequence, there is a concern that the oxidized layer 20 cannot prevent contact failure between the air chamber 141 and the measurement gas chamber 142 through the metal sealing member 2.

As mentioned above, when the metal sealing member includes 1-10 wt % Cr, the member can hermetically the air chamber 141 and the measurement gas chamber 142.

Furthermore, in the SAMPLE E4, when the metal sealing member 20 includes 42 wt % Ni, a difference in the coefficient of thermal expansion between the base material of the metal sealing member 2 and the oxidized layer 20 thereof can become sufficiently small. Therefore, peeling the oxidized layer 20 from the based material of the sealing metal member 20 can be prevented.

Example 4

Figure 6:
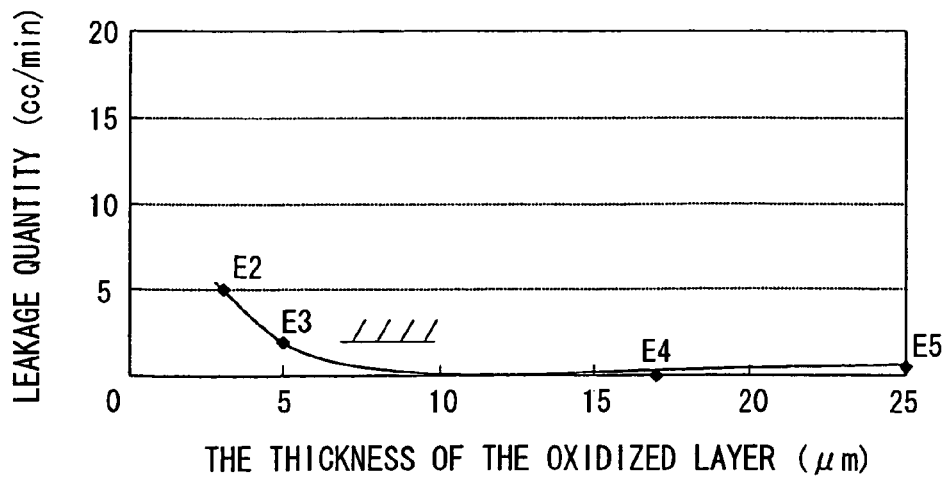
FIG. 6 is a graph representing a relationship between a leakage quantity of measurement gas and a thickness of an oxidized layer formed on a surface of a metal sealing member according to a fourth example embodiment of the present invention.
Figure 7:
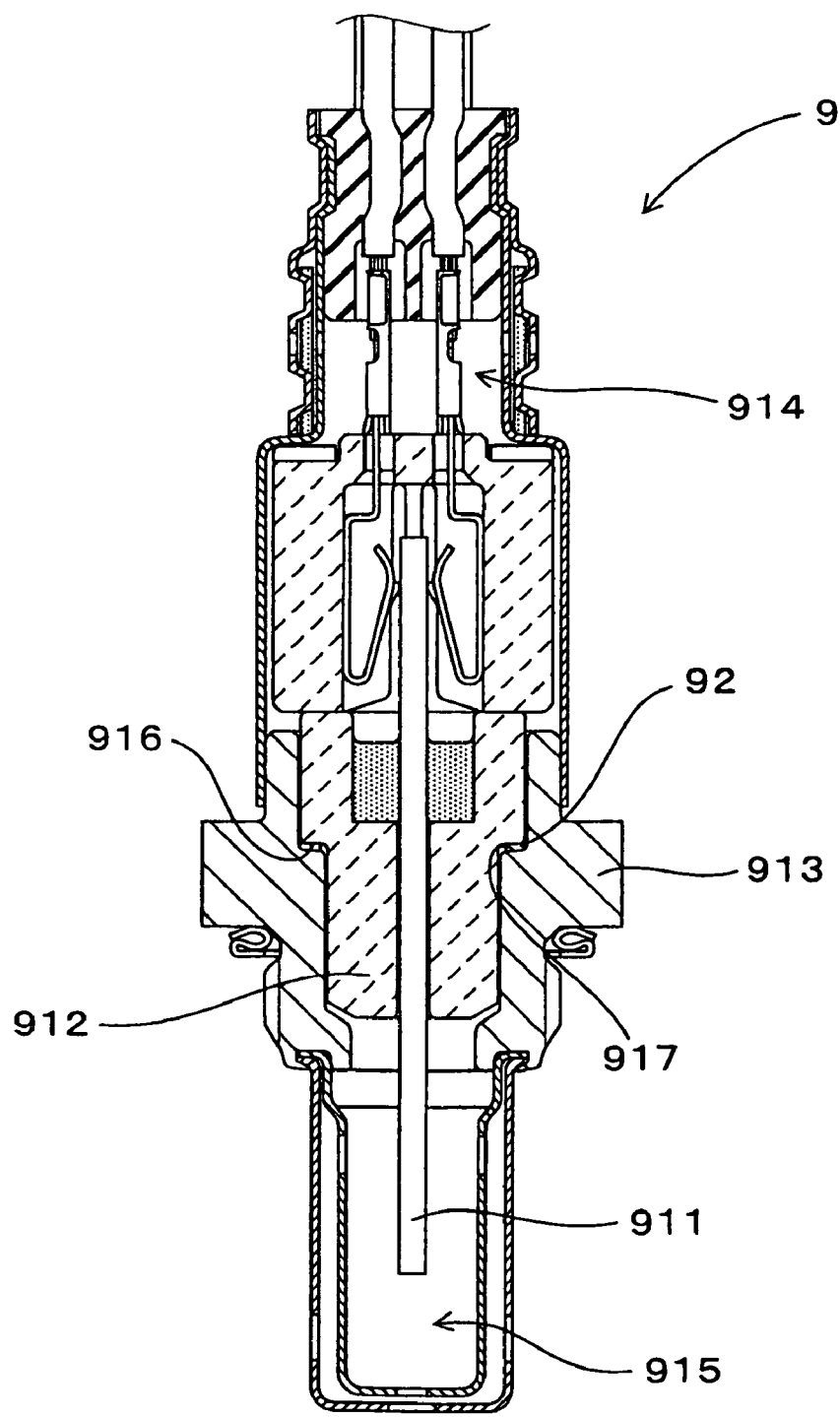
FIG. 7 is a longitudinal sectional view of a gas sensor according to a prior art.
Figure 8:
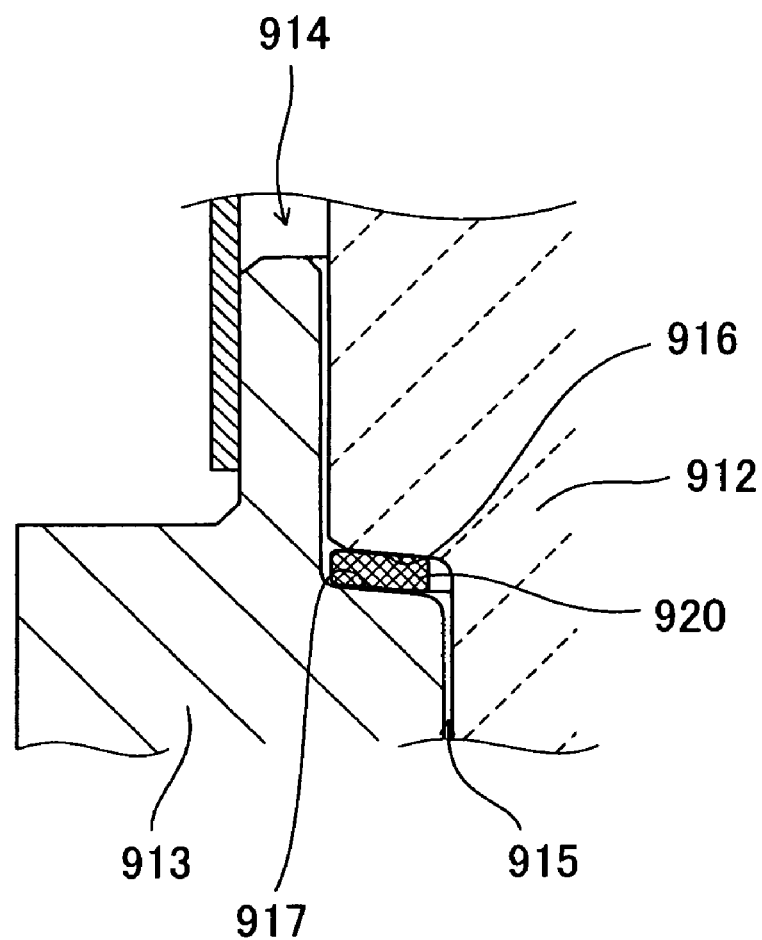
FIG. 8 schematically illustrates, in cross section, a metal packing ring between a first insulation porcelain and a housing accordance to the prior art.

As shown in FIG. 6, this example describes a relationship between a leakage quantity and a thickness of the oxidized layer 20 using the SAMPLES E2-E5 of Example 3.

The thickness of the oxidized layers 20 are measured by investigation of the cross-section of the each metal sealing members 2, after the above endurance test.

The thickness of each metal sealing member 2 is calculated from the average thickness of the first insulation porcelain side of the metal sealing member 2 and that of the housing side thereof. The amount of the calculated members is ten pieces of the each SAMPLEs. FIG. 6 shows that the results of the investigation plotted in a graph in which the thickness of the oxidized layers 20 is the horizontal axis and the leakage quantity of Example 3 is the vertical axis.

As shown in FIG. 6, when the thickness of the oxidized layer 20 is less than 5 μm, the leakage quantity is more than 2 CC/min. As shown in TABLE 1 and FIG. 5, SAMPLES E2-E3 in which a large amount of Cr is added, have a thin oxidized layer thickness and a large leakage quantity.

More specifically, when the thickness of those oxidized layers is 5 μm or less, the oxidized layer 20 can have the protecting function for the metal sealing member 2. However, it is difficult for the contacting property between the air chamber 141 and the measurement gas chamber 142 to be ensured.

The ratio of the area of the 5 μm or more thickness of the oxidized layer 20 to the gross area of the contact surfaces of the SAMPLE 4, between the metal sealing member and the first insulation porcelain and between the metal sealing member and the housing, was investigated. The result of the investigation was that the oxidized layer 20 was formed in 30% or more of the contact surface.

More specifically, when the ratio of the area having 5 μm or more thickness of the oxidized layer to the gross area of the contact surfaces is less than 30%, the oxidized layer can not sufficiently prevent oxidized corrosion of the metal sealing member, and the contacting property between the air chamber 141 and the measurement gas chamber 142 can not be ensured.

On the other hand, when the area having 5 μm or more of thickness of the oxidized layer 20 on the contact surface is 30% or more, this invention can sufficiently provide the function of this invention.

Although the present invention has been fully described in connection with the preferred embodiments thereof with reference to the accompanying drawings, it is to be noted that various changes and modifications will become apparent to those skilled in the art.

What is claimed is:

1. A gas sensor comprising:
   a gas sensing element detecting the concentration of a particular gas contained in measurement gas;
   a housing holding said gas sensing element;
   a seat surface formed on an inner surface of said housing receiving a contacting surface formed on an outside surface of said gas sensing element;
   a metal sealing member interposed between said seat surface of said housing and said a contacting surface of said gas sensing element to hermetically define an air chamber in which a base end side of said gas sensing element is disposed and a measurement gas chamber in which a top end side of said gas sensing element is disposed; and
   said metal sealing of an oxidized layer which is comprised a chrome oxide layer and a ferric oxide layer and has a thickness of at least 5 μm, after said metal sealing member is exposed to environmental conditions as follows: a cycle of changing temperature from 300° C. or less to 600° C. or more repeated 1000 times and more, and total hours at 600° C. or more is fifty hours or more.

2. A gas sensor as in claim 1 wherein the ratio of the area of 5 μm or more thickness of said oxidized layer to the gross area of said contact surface, between said metal sealing member and said first insulation porcelain and between said metal sealing member and the housing, is 30% or more.

3. A gas sensor comprising:
   a gas sensing element detecting the concentration of a particular gas contained in measurement gas;
   a first insulation porcelain holding therein said gas sensing element;
   a housing holding said first insulation porcelain on an inner surface thereof;
   a seat surface formed on said inner surface of said housing receiving a contacting surface formed on an outside surface of said first insulation porcelain; and
   a metal sealing member interposed between said seat surface of said housing and said contacting surface of said first insulation porcelain to hermetically define an air chamber in which a base end side of said gas sensing element is disposed and a measurement gas chamber in which a top end side of said gas sensing element is disposed;
   said metal sealing member having an oxidized layer comprised of a chrome oxide layer and a ferric oxide layer and has a thickness of at least 5 μm after said metal sealing member is exposed to environmental conditions as follows: a cycle of changing temperature from 300° C. or less to 600° C. or more repeated 1000 times and more, and total hours at 600° C. or more is fifty hours or more.

4. A gas sensor as in claim 3 wherein the ratio of the area of 5 μm or more thickness of said oxidized layer to the gross area of each said contact surface, between said metal sealing member and said first insulation porcelain and between said metal sealing member and said housing, is 30% or more.

* * * * *